(12) United States Patent
Yano et al.

(10) Patent No.: US 6,773,881 B2
(45) Date of Patent: Aug. 10, 2004

(54) METHODS OF MODULATING HAIR GROWTH

(75) Inventors: Kiichiro Yano, Fukuoka (JP); Michael Detmar, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/813,640

(22) Filed: Mar. 21, 2001

(65) Prior Publication Data

US 2002/0062835 A1 May 30, 2002

Related U.S. Application Data

(60) Provisional application No. 60/193,597, filed on Mar. 31, 2000.

(51) Int. Cl.[7] ................................................. C12Q 1/68
(52) U.S. Cl. ............................. 435/6; 435/363; 435/371
(58) Field of Search ............................ 435/6, 363, 371; 424/9.1

(56) References Cited

U.S. PATENT DOCUMENTS 5,480,975 A    1/1996   Goldberg et al. ........... 530/399
6,159,950 A   12/2000   Crystal et al. ................ 514/44

OTHER PUBLICATIONS

Lachgar, S. et al. Minoxidil upregulates the expression of vascular endothelial graowth fctor in human hair dermal papilla cells. British Journal of Dermatology 1998; vol. 138, pp. 407–411.*

Kozlowska, U. et al. Expression of vascular endothelial growth factor (VEGF) in various compartments of the human hair follicle. Archives of Dermatology Research 1998; vol. 290, pp. 661–668.*

Brown et al., "Increased Expression of Vascular Permeability Factor . . . ", May 1995, *J. Invest. Dermatol.*, vol. 104, No. 5:744–749.

Cormia et al., "Circulatory Changes in Alopecia", Nov. 1961, *Arch. Dermatol.*, vol. 84:772–778.

Detmar et al., "Increased Microvascular Density and Enhanced . . . ", Jul. 1998, *J. Invest. Dermatol.*, vol. 111, No. 1:1–6.

Napoleone Ferrara, "VEGF: an update on biological and therapeutic aspects", (2000) *Curr.Opin.Biotech. 2000*, vol. 11;617–624.

Hardy et al., "The secret life of the hair follicle", Feb. 1992, *Trends in Genetics*, vol. 8, No. 2:55–61.

Hopkins et al., "Controlled delivery of vascular endothelial growth factor . . . ", May 1998, *J. Vasc. Surg.*, vol. 27, No. 5;886–895.

Kozolowska et al., "Expression of vascular endotheial growth factor . . . ", (1998) *Arch. Dermatol. Res.*, vol. 290;661–668.

Lachgar et al., "Minioxidil upregulates the expression of vascular . . . ", Mar. 1998, *Br. J. Dermatol*, 138(3):407–11.

Paus et al., "The Biology of hair Follicles", Aug. 1999, *New Engl. J. Med.*, vol. 341, No. 7;491–497.

Yano et al., "Control of hair growth and follicle size . . . ", Feb. 2001, *J. Clin. Invest*, vol. 107, No. 4:409–417.

\* cited by examiner

*Primary Examiner*—Dave T. Nguyen
*Assistant Examiner*—J. Eric Angell
(74) *Attorney, Agent, or Firm*—Fish & Richardson P.C.

(57) ABSTRACT

A method of modulating hair growth and/or hair thickness. The method includes modulating VEGF activity, e.g., modulating VEGF gene expression and/or modulating VEGF protein production and/or activity, to modulate hair growth and/or thickness. The methods can be used to either promote or inhibit hair growth or hair thickness in a subject.

26 Claims, 6 Drawing Sheets

METHODS OF MODULATING HAIR GROWTH

This application claims benefits of Provisional application 60/193,597 filed Mar. 31, 2000.

BACKGROUND OF THE INVENTION

The hair follicle undergoes a life-long transformation from a resting phase (telogen) to a growth phase (anagen) with rapid proliferation of follicular keratinocytes and elongation and thickening of the hair shaft. Anagen phase is followed by regression phase (catagen) leading to involution of the hair follicle (telogen) which continues until a new hair shaft is generated in the existing follicle during the subsequent anagen phase. Hardy et al. (1992) *Trends in Genetics* 8:55–61. These cyclic changes involve rapid remodeling of both epithelial and dermal components of the hair follicle.

SUMMARY OF THE INVENTION

The invention is based, in part, on the discovery that increased perifollicular vascularization promotes hair growth and that expression of VEGF by follicular keratinocytes leads to increased perifollicular vascularization. In addition, it was found that increasing the level of VEGF expression resulted in accelerated hair regrowth and increased hair follicle size, which leads to hair thickening. It was also found that by inhibiting the levels of VEGF, hair growth and hair thickening can be reduced.

Accordingly, in one aspect, the invention features a method of modulating hair growth and/or hair thickness. The method includes modulating VEGF protein, e.g., modulating VEGF gene expression and/or modulating VEGF protein production and/or activity, to thereby modulate hair growth and/or thickness.

In another aspect, the invention features a method of promoting hair growth in a subject. The method includes increasing the VEGF activity, e.g., increasing the level of VEGF protein, e.g., increasing the levels of VEGF gene expression and/or increasing VEGF protein production and/or activity, to thereby promote hair growth.

In a preferred embodiment, VEGF activity is increased by administering an agent which increases the level of VEGF protein. An agent which increases the level of VEGF protein can be one or more of: a VEGF polypeptide or a functional fragment or analog thereof; a nucleotide sequence encoding a VEGF polypeptide or functional fragment or analog thereof; an agent which increases VEGF nucleic acid expression, e.g., a transition metal ion, or a small molecule which binds to the promoter region of VEGF.

In a preferred embodiment, VEGF is increased by administering, e.g., introducing, a nucleotide sequence encoding a VEGF polypeptide or functional fragment or analog thereof, into a particular cell, e.g., a keratinocyte, e.g., a follicular keratinocyte, in the subject. The nucleotide sequence can be a genomic sequence or a cDNA sequence. The nucleotide sequence can include: a VEGF coding region; a promoter sequence, e.g., a promoter sequence from a VEGF gene or from another gene; an enhancer sequence, e.g., 5' untranslated region (UTR), e.g., a 5' UTR from a VEGF gene or from another gene, a 3' UTR, e.g., a 3' UTR from a VEGF gene or from another gene; a polyadenylation site; an insulator sequence.

In another preferred embodiment, the agent is a compound, e.g., a small molecule, which increases VEGF expression. For example, the molecule can be a transition metal ion, e.g., manganese, cobalt, nickel, or combinations thereof. In another preferred embodiment, the agent is a polypeptide other than VEGF which increases VEGF expression. For example, the agent can be a cytokine, e.g., interleukin-1, or a growth factors, e.g., transforming growth factor-α, epidermal growth factor.

In another preferred embodiment, the level of VEGF protein is increased by increasing the level of expression of an endogenous VEGF coding sequence, e.g., by increasing transcription of the VEGF coding sequence. In a preferred embodiment, transcription of the VEGF gene is increased by: altering the regulatory sequences of the endogenous VEGF gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the VEGF gene to be transcribed more efficiently.

In another preferred embodiment, the method can include introducing a cell, e.g., a cell which expresses and preferably secretes a VEGF protein, into a subject. In a preferred embodiment, the cell has been genetically modified to express a VEGF protein, a fragment or an analog thereof, or a protein other than VEGF which causes an increase in the levels of VEGF. The cell can be an autologous, allogeneic, or xenogeneic cell, but is preferably autologous. In a preferred embodiment, the cell is encapsulated, e.g., in a gel or biocompatible mesh, which is introduced into the subject. The cell can be any cell type, e.g., a fibroblast, a keratinocyte, an epithelial cell, an endothelial cell. Preferably the cell is a keratinocyte, e.g., a follicular keratinocyte. The cell can be introduced into a subject to increase the level of VEGF protein.

In a preferred embodiment, the agent which increases the level of VEGF protein is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the VEGF protein level is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair growth is promoted on: the subject's scalp; the subject's face, e.g., beard and/or mustache facial hair growth is promoted.

In a preferred embodiment, the subject has an insufficient amount of hair or an insufficient rate of hair growth. In a preferred embodiment, the subject suffers from genetic pattern baldness; suffers from a hormonal disorder which decreases hair growth; has received a treatment, e.g., radiation, or chemotherapy, or a drug which inhibits hair growth; or has had a surgical procedure, e.g., skin graft, which is in need of hair growth.

In another aspect, the invention features a method of enhancing hair thickness. The method includes increasing the level of VEGF protein, e.g., increasing the levels of VEGF gene expression and/or increasing VEGF protein production and/or activity, to thereby promote thickening of the hair.

In a preferred embodiment, VEGF activity is increased by administering an agent which increases the level of VEGF protein. An agent which increases the level of VEGF protein can be one or more of: a VEGF polypeptide or a functional fragment or analog thereof; a nucleotide sequence encoding a VEGF polypeptide or functional fragment or analog thereof; an agent which increases VEGF nucleic acid expression, e.g., a transition metal ion, or a small molecule which binds to the promoter region of VEGF.

In a preferred embodiment, VEGF is increased by administering, e.g., introducing, a nucleotide sequence encoding a VEGF polypeptide or functional fragment or analog thereof, into a particular cell, e.g., a keratinocyte, e.g., a follicular keratinocyte, in the subject. The nucleotide sequence can be a genomic sequence or a cDNA sequence. The nucleotide sequence can include: a VEGF coding region; a promoter sequence, e.g., a promoter sequence from a VEGF gene or from another gene; an enhancer sequence, e.g., 5' untranslated region (UTR), e.g., a 5' UTR from a VEGF gene or from another gene, a 3' UTR, e.g., a 3' UTR from a VEGF gene or from another gene; a polyadenylation site; an insulator sequence.

In preferred embodiment, the agent is a compound, e.g., a small molecule, which increases VEGF expression. For example, the molecule can be a transition metal ion, e.g., manganese, cobalt, nickel, or combinations thereof, or an inducer of reactive oxygen species. In another preferred embodiment, the agent is a polypeptide other than VEGF which increases VEGF expression. For example, the agent can be a cytokine, e.g., interleukin-1, or a growth factors, e.g., transforming growth factor-α, epidermal growth factor.

In another preferred embodiment, the level of VEGF protein is increased by increasing the level of expression of an endogenous VEGF gene, e.g., by increasing transcription of the VEGF gene. In a preferred embodiment, transcription of the VEGF gene is increased by: altering the regulatory sequences of the endogenous VEGF gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the VEGF gene to be transcribed more efficiently.

In another preferred embodiment, the method can include introducing a cell, e.g., a cell which expresses and preferably secretes a VEGF protein, into a subject. In a preferred embodiment, the cell has been genetically modified to express a VEGF protein, or a fragment or an analog thereof. The cell can be an autologous, allogeneic, or xenogeneic cell, but is preferably autologous. The cell can be any cell type, e.g., a fibroblast, a keratinocyte, an epithelial cell, an endothelial cell. Preferably the cell is a keratinocyte, e.g., a follicular keratinocyte. The cell can be encapsulated, e.g., in a gel or biocompatible mesh. The cell can be introduced into a subject to increase the level of VEGF protein.

In a preferred embodiment, the agent which increases the level of VEGF protein is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the VEGF protein level is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair thickness is promoted on: the subject's scalp; the subject's face, e.g., beard and/or mustache.

In a preferred embodiment, the subject has: fine or limp hair; an insufficient amount of hair; an insufficient rate of hair growth.

In another aspect, the invention features a method of inhibiting hair growth in a subject. The method includes inhibiting the level of VEGF activity, e.g., inhibiting the level of VEGF protein, decreasing the levels of VEGF gene expression and/or decreasing VEGF protein production and/or activity, in the subject.

In a preferred embodiment, VEGF is inhibited by administering an agent which inhibits VEGF. An agent which inhibits VEGF can be one or more of: a VEGF nucleic acid molecule which can bind to a cellular VEGF nucleic acid sequence, e.g., mRNA, and inhibit expression of the protein, e.g., an antisense molecule or VEGF ribozyme; an antibody that specifically binds to VEGF protein, e.g., an antibody that disrupts VEGF's ability to bind to its natural cellular target; an agent which decreases VEGF gene expression, e.g., a small molecule which binds the promoter of VEGF.

In another preferred embodiment, VEGF activity is inhibited by decreasing the level of expression of an endogenous VEGF gene, e.g., by decreasing transcription of the VEGF gene. In a preferred embodiment, transcription of the VEGF gene can be decreased by: altering the regulatory sequences of the endogenous VEGF gene, e.g., by the addition of a negative regulatory sequence (such as a DNA-binding site for a transcriptional repressor).

In another preferred embodiment, the agent is a compound, e.g., small molecule, which is known to inhibit VEGF, e.g., a transition metal.

In a preferred embodiment, the agent which inhibits VEGF expression is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the VEGF protein level is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair growth is inhibited on: the subject's scalp; the subject's face, e.g., beard and/or mustache facial hair growth or eyebrow growth is inhibited; the subject's body hair growth is inhibited, e.g., hair growth is inhibited on the subject's back, legs, chest, armpits.

In a preferred embodiment, the method further includes the removal of hair, e.g., by plucking, shaving or application of a depilatory. In a preferred embodiment, hair is removed sequentially or simultaneously with the inhibition VEGF expression. Preferably, hair is removed prior to the inhibition of VEGF expression.

In another aspect, the invention features a method of reducing hair thickness. The method includes inhibiting the level of VEGF protein, e.g., decreasing the levels of VEGF gene expression and/or decreasing VEGF protein production and/or activity in the subject.

In a preferred embodiment, VEGF is inhibited by administering an agent which inhibits VEGF. An agent which inhibits VEGF can be one or more of: a VEGF nucleic acid molecule which can bind to a cellular VEGF nucleic acid sequence, e.g., mRNA, and inhibit expression of the protein, e.g., an antisense molecule or VEGF ribozyme; an antibody that specifically binds to VEGF protein, e.g., an antibody that disrupts VEGF's ability to bind to its natural cellular target; an agent which decreases VEGF gene expression, e.g., a small molecule which binds the promoter of VEGF.

In another preferred embodiment, VEGF is inhibited by decreasing the level of expression of an endogenous VEGF gene, e.g., by decreasing transcription of the VEGF gene. In a preferred embodiment, transcription of the VEGF gene can be decreased by: altering the regulatory sequences of the endogenous VEGF gene, e.g., by the addition of a negative regulatory sequence (such as a DNA-binding site for a transcriptional repressor).

In another preferred embodiment, the agent is a compound, e.g., small molecule, which is known to inhibit VEGF.

In a preferred embodiment, the agent which inhibits VEGF expression is administered, e.g., by topically administering the agent; systemically administering the agent; orally administering the agent; or injecting the agent, preferably dermally or subcutaneously. In preferred embodiments, the compound is administered using a suitable delivery vehicle, for example, a surfactant or an agent which increases permeability in the skin, e.g., an SDS or DMSO containing formulation. Preferably, the agent is included in a composition for topical use, e.g., the composition is a gel, cream, or liquid. In a preferred embodiment, the agent is administered: by continuous administration, e.g., the agent is administered with sufficient frequency such that the affect on the VEGF protein level is maintained for a selected period, e.g., 10, 20, 30, 50, 90, 180, 365 days or more. In another preferred embodiment, administration of the agent is repeated, e.g., is repeated at least 1, 2, 3, 5, 10, 20 or more times.

In a preferred embodiment, hair thickness is reduced on: the subject's scalp; the subject's face, e.g., beard and/or mustache or eyebrows; the subject's body, e.g., on the subject's back, legs, chest, armpits.

In a preferred embodiment, the method further includes the removal of hair, e.g., by plucking, shaving or application of a depilatory. In a preferred embodiment, hair is removed sequentially or simultaneously with the inhibition VEGF expression. Preferably, hair is removed prior to the inhibition of VEGF expression.

In another aspect, the invention features a method of evaluating the status of hair growth/hair loss in a subject. The method includes evaluating, e.g., detecting, the presence or absence of a genetic lesion in a VEGF gene, or evaluating, e.g., detecting, misexpression of the VEGF gene.

In one embodiment, the method includes evaluating whether a subject is at risk for hair loss. The method includes evaluating, e.g., detecting, a genetic lesion in a VEGF gene, or evaluating, e.g., detecting, underexpression of the VEGF gene, to thereby determine if a subject is at risk for hair loss.

In preferred embodiment, the method includes evaluating in a sample of cells from the subject for the presence or absence of a genetic lesion, e.g., a mutation in the gene encoding a VEGF protein. The presence of a genetic lesion is indicative of a risk of hair loss in a subject. The cell sample can be of any cell type, e.g., a fibroblast, a keratinocyte, an epithelial cell, an endothelial cell, a glial cell, a neural cell, a lymphocyte, a bone marrow cell, and a muscle cell.

In another preferred embodiment, the method includes evaluating in a sample of cells, e.g., a sample of keratinocytes, e.g., follicular keratinocytes, of a subject, for the expression levels of the VEGF to determine underexpression. Underexpression of VEGF can be indicative of a risk of hair loss.

In a preferred embodiment, the genetic lesions is evaluated by contacting the sample with a nucleic acid probe capable of hybridizing to VEGF mRNA, e.g., a labeled probe. In another preferred embodiment, expression of VEGF is evaluated with an antibody capable of binding to VEGF protein, e.g., a labeled antibody.

In another embodiment, the method includes evaluating hair growth in a subject. The method includes evaluating, e.g., detecting, absence or presence of a genetic lesion in a VEGF gene, or evaluating, e.g., detecting, overexpression of the VEGF gene, to thereby evaluate whether hair growth is likely in a subject.

In a preferred embodiment, the method includes evaluating in a sample of cells from the subject for the presence or absence of a genetic lesion, e.g., a mutation in the gene encoding a VEGF protein. The absence of a genetic lesion can be indicative of a potential for hair growth. The cell sample can be of any cell type, e.g., a fibroblast, a keratinocyte, an epithelial cell, an endothelial cell, a glial cell, a neural cell, a lymphocyte, a bone marrow cell, and a muscle cell.

In another preferred embodiment, the method includes evaluating in a sample of cells, e.g., a sample of keratinocytes, e.g., follicular keratinocytes, of a subject, for the expression levels of VEGF to determine expression. Normal levels of VEGF expression or overexpression of VEGF can be indicative of a potential for hair growth.

In a preferred embodiment, the genetic lesions is evaluated by contacting the sample with a nucleic acid probe capable of hybridizing to VEGF mRNA, e.g., a labeled probe. In another preferred embodiment, expression of VEGF is evaluated with an antibody capable of binding to VEGF protein, e.g., a labeled antibody.

In another aspect, the invention features a method of evaluating the ability of a keratinocyte to induce growth or hair loss in a subject. The method includes evaluating, e.g., detecting, the presence or absence of a genetic lesion in a VEGF gene, or evaluating, e.g., detecting, misexpression of the VEGF gene.

In a preferred embodiment, the keratinocyte is evaluated in vitro.

In one embodiment, the method includes evaluating the ability of a keratinocyte to induce hair loss. The method includes evaluating, e.g., detecting, a genetic lesion in a VEGF gene, or evaluating, e.g., detecting, underexpression of the VEGF gene.

In preferred embodiment, the method includes evaluating a sample of keratinocytes, e.g., follicular kertinocytes, for the presence or absence of a genetic lesion, e.g., a mutation in the gene encoding a VEGF protein. The presence of a genetic lesion is indicative of a risk of hair loss in a subject.

In another preferred embodiment, the method includes evaluating a sample of keratinocytes, e.g., follicular keratinocytes, of a subject, for the expression levels of the VEGF to determine underexpression. Underexpression of VEGF is indicative of a risk of hair loss.

In a preferred embodiment, the genetic lesions is evaluated by contacting the sample with a nucleic acid probe capable of hybridizing to VEGF mRNA, e.g., a labeled probe. In another preferred embodiment, expression of VEGF is evaluated with an antibody capable of binding to VEGF protein, e.g., a labeled antibody.

In another embodiment, the method includes evaluating the ability of a kertinocyte to induce hair growth. The method includes evaluating, e.g., detecting, absence or presence of a genetic lesion in a VEGF gene, or evaluating, e.g., detecting, overexpression of the VEGF gene.

In a preferred embodiment, the method includes evaluating in a sample of keratinocytes, e.g., follicular keratinocytes, from the subject for the presence or absence of a genetic lesion, e.g., a mutation in the gene encoding a VEGF protein. The absence of a genetic lesion is indicative of a potential for hair growth.

In another preferred embodiment, the method includes evaluating in a sample of keratinocytes, e.g., follicular keratinocytes, of a subject, for the expression levels of VEGF to determine expression. Normal levels of VEGF expression or overexpression of VEGF is indicative of a potential for hair growth.

In a preferred embodiment, the genetic lesions is evaluated by contacting the sample with a nucleic acid probe capable of hybridizing to VEGF mRNA, e.g., a labeled probe. In another preferred embodiment, expression of VEGF is evaluated with an antibody capable of binding to VEGF protein, e.g., a labeled antibody.

In another aspect, the invention features, a method of evaluating a candidate compound. The method is useful for identifying a compound, e.g., a VEGF polypeptide, or a fragment or analog thereof, which can be used to modulate hair growth and/or thickness. The method can evaluate the ability of the compound to increase VEGF activity, e.g., by increasing the expression of the VEGF gene or the activity of the VEGF protein. The method includes: providing a cell, a tissue, or a subject, treating the cell or the tissue, or the subject with a candidate compound; and determining the level of VEGF RNA, VEGF DNA or VEGF protein. The method can further include evaluating a control cell, tissue or subject, e.g., an identical cell which, e.g., is not treated with the candidate compound. An increase in the amount of VEGF activity in the cell tissue or subject treated with the compound in comparison to the control is indicative of a useful compound, e.g., a compound useful for promoting hair growth and/or thickness.

In a preferred embodiment the compound is a fragment or an analog of VEGF.

In a preferred embodiment, the cell is a keratinocyte, e.g., a follicular keratinocyte.

The invention also features methods for identifying a compound which interacts with a VEGF protein. In a preferred embodiment, the method can include the steps of contacting the VEGF protein with the compound under conditions which allow binding of the compound to the VEGF protein to form a complex, and detecting the formation of a complex of the VEGF protein and the compound in which the ability of the compound to bind to the VEGF protein is indicated by the presence of the compound in the complex. Using such methods, compounds can be identified which modulate, e.g., promote or inhibit, hair growth and/or hair thickness. Methods for identifying a compound or agent can be performed, for example, using a cell free assay. For example, VEGF can be immobilized to a suitable substrate, e.g., glutathione sepharose beads or glutathione derivatized microtitre plates, using a fusion protein which allows for VEGF to bind to the substrate, e.g., a glutathoine-S-transferase/VEGF fusion protein.

In a preferred embodiment the compound is a fragment or an analog of VEGF.

In a preferred embodiment, the compound is a transition metal ion.

In a preferred embodiment, the method further includes providing a cell, a tissue, or a subject, treating the cell or the tissue, or the subject with the identified compound; and determining the level of VEGF RNA, VEGF DNA or VEGF protein. In a preferred embodiment, the cell is a keratinocyte, e.g., a follicular keratinocyte.

In another embodiment, a compound which interacts with a VEGF protein can be identified using a cell-based assay. These methods can include identifying a compound based on its ability to promote, a biological activity of VEGF. In a preferred embodiment, the compound modulates a biological activity of VEGF, e.g., the compound modulates perifollicular vascularization. In a preferred embodiment, the compound is a fragment or an analog of VEGF.

In another aspect, the invention features, a method for identifying compounds which increase VEGF nucleic acid expression. In a preferred embodiment, nucleic acid expression can be evaluated using a nucleic acid probe, e.g., a labeled probe, capable of hybridizing to a VEGF nucleic acid molecule, e.g., VEGF mRNA. In another preferred embodiment, VEGF nucleic acid expression, e.g., DNA expression, can be evaluated by contacting a compound with a VEGF nucleic acid molecule, e.g., a regulatory sequence of a VEGF nucleic acid molecule, and evaluating VEGF transcription, in vitro or in vivo. VEGF transcription can be evaluated, for example, by detecting the production of VEGF protein, e.g., using an antibody, e.g., a labeled antibody, or by determining a cell activity, e.g., using a marker gene, e.g., a lacZ gene or green fluorescence protein (GFP) gene, fused to the regulatory sequence of VEGF and following production of the marker.

In a preferred embodiment, the compound is a fragment or an analog of VEGF.

In a preferred embodiment, the compound is a transition metal ion.

In a preferred embodiment, VEGF transcription is evaluated in a cell, e.g., a keratinocyte, e.g., a follicular keratinocyte.

A "treatment", as used herein, includes any therapeutic treatment, e.g., the administration of a therapeutic agent or substance, e.g., a drug.

As used herein, the term "subject" refers an animal, e.g., a mammal, e.g., a human. The mammal can be a human or non-human mammal, e.g., a swine, a bird, a cat, a dog, a monkey, a goat, or a rodent, e.g., a rat or a mouse. The subject can be a transgenic animal, e.g., a transgenic rodent, e.g., a transgenic rat or mouse.

"Regulatory sequence" refers to any or all of the DNA sequences that controls gene expression. An example of a regulatory sequence includes: a promoter, a positive regulatory element (such as an enhancer or a DNA-binding site for a transcriptional activator); a negative regulatory element (such as a DNA-binding site for a transcriptional repressor) and an insulator.

"Heterologous" refers to DNA or tissue which is derived from a different species.

"Heterologous regulatory sequence" refers to a sequence which is not the normal regulatory sequence of that gene.

"Misexpression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

The terms "peptides", "proteins", and "polypeptides" are used interchangeably herein, The term "small molecule", as used herein, includes peptides, peptidomimetics, or non-peptidic compounds, such as organic molecules, having a molecular weight less than 2,000, preferably less than 1,000.

Other features and advantages of the invention will be apparent from the following detailed description, and from the claims.

BRIEF DESCRIPTION OF THE DRAWINGS

FIG. 1A is a graph of the relative areas covered by blood vessels during early anagen (EA) (day 1), mid-anagen (MA)(day 5), late anagen (LA) (day 12), catagen (C) (day 18) and telogen (T) (day 22). FIGS. 1B and 1C are similar graphs demonstrating changes in vesicle size (FIG. 1B) and vessel density (FIG. 1C) during the hair cycle. FIGS. 1D–1F show changes in epidermal thickness (FIG. 1D), hair follicle diameter (FIG. 1E), and dermal thickness (FIG. 1F) during day 1–12 (D1–D12) of anagen. $*P<0.05$; $P<0.01$; $*P<0.001$, two-sided unpaired Student's t test.

FIG. 5A shows hair bulb diameter of control treated and anti-VEGF treated mice 12 days after depilation. FIG. 5B is a graph of perifollicular vessel size in control treated and anti-VEGF treated mice. FIG. 5C is a graph showing relative area covered by vessels in control treated and anti-VEGF treated mice. $***P<0.001$, two-sided unpaired Student's t test.

DETAILED DESCRIPTION

Figure 1:
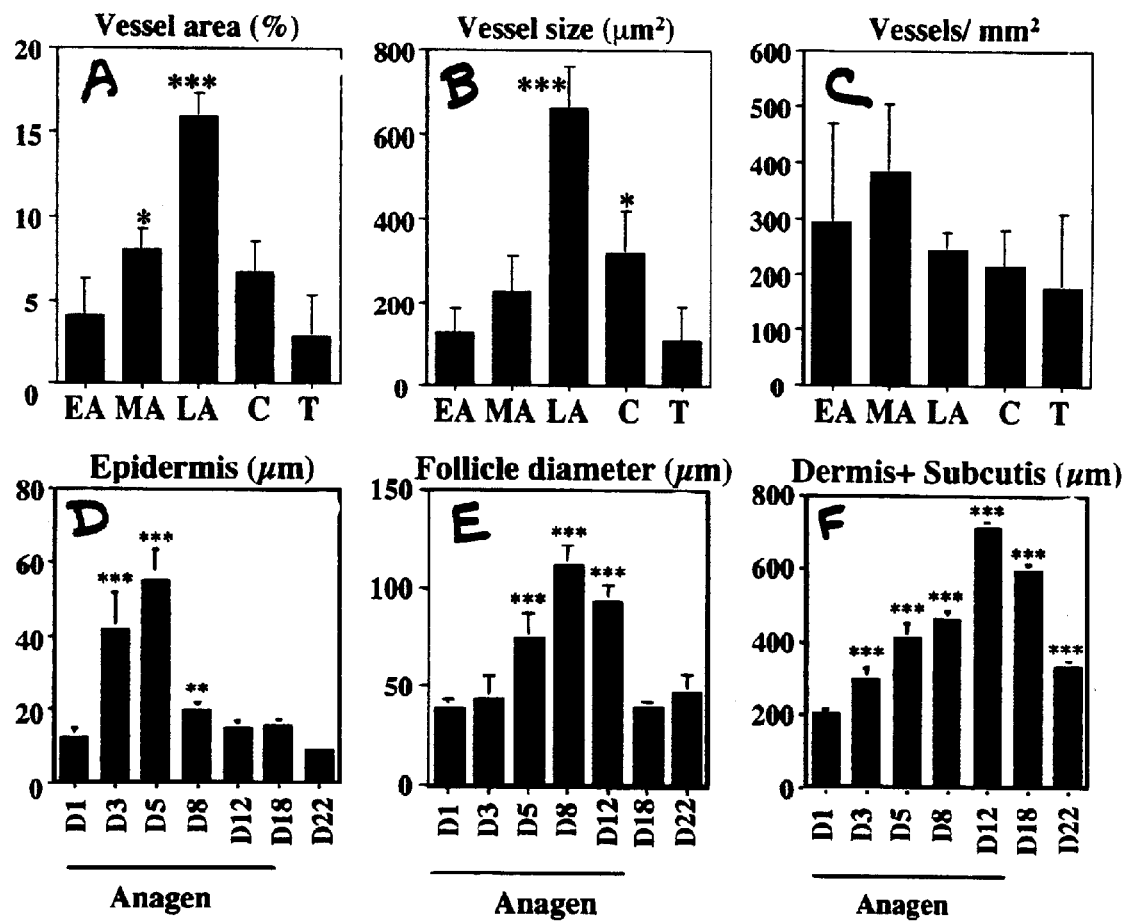
FIG. 1 demonstrates vascular changes during induced murine hair cycle.

The present invention is based, in part, on the discovery that timed expression of VEGF by follicular keratinocytes provides the mechanism by which the hair follicle meets its rapidly changing, high metabolic demands and which leads to increased perifollicular vascularization.

The hair follicle is characterized by rapid cyclic changes of size and shape. A dramatic increase in perifollicular vascularization during the growth phase (anagen) of the murine hair cycle was found, followed by complete regression of angiogenic blood vessels during involution (catagen) and the resting (telogen) phase. Perifollicular angiogenesis was temporally and spatially correlated with pronounced upregulation of vascular endothelial growth factor (VEGF) mRNA expression by follicular keratinocytes. Targeted overexpression of VEGF in hair follicles of transgenic mice potently induced perifollicular vascularization, resulting in accelerated hair regrowth after depilation and increased size of hair follicles. Conversely, blockade of VEGF by systemic treatment with a neutralizing anti-VEGF antibody resulted in hair growth retardation and, additionally, in size reduction of hair follicles. These results demonstrate that improved vascularization promotes hair growth and increases hair follicle size and that improved vascularization can be obtained by overexpression of VEGF, e.g., targeted overexpression of VEGF in keratinocytes.

Morphogenic Analysis of Hair Follicle Development & Cycling

Angiogenesis was first studied during normal postnatal hair follicle development and depilation-induced adult hair cycling by computer-assisted morphometric analyses of back skin sections. See Streit et al. (1999) *Proc. Natl Acad. Sci. USA* 96:14888–14893. For examination of the postnatal hair cycles, C57BL/6 mice (Charles River) were sacrificed at postpartal days 1, 3, 4, 8, 12, 18, and 22. Back skin was harvested parallel to the paravertebral line, and skin samples were either snap frozen in liquid nitrogen or fixed in 4% paraformaldehyde as described in Detmar et al. (1998) *J. Invest. Dermatol.* 111: 1–6. Hair cycling was induced in the back skin of eight-week-old female mice by depilation as described Paus et al. (1990) *Br. J. Dermatol.* 122:777–784, leading to synchronized development of anagen hair follicles. Tissues were harvested at the same time points as described above.

The back sections were stained for PECAM-1 (CD31), and endothelial junction molecule as described in Dejana et al. (1995) FASEB J. 9:910–918, obtained over a 22-day period that covered all phases of the murine hair cycle from early anagen to telogen. Briefly, immunohistochemical stainings for CD31 were performed on 5 µm frozen sections as described Streit et al., supra, using a monoclonal rat anti-mouse CD31 antibody (Pharmingen). Representative sections obtained from three mice for each time point were analyzed, using a Nikon E-600 microscope (Nikon). Images were captured with a Spot digital camera (Diagnostic Instruments), and morphometric analyses were performed using the IP-LAB software (Scanalytics Inc.). Three different fields in each section were examined at 60× magnification, and the number of vessels per $mm^2$, the average vessel size, and the relative area occupied by blood vessels were determined as described Streit et al., supra, within an area of 30 µm distance of individual hair follicles.

As shown in FIG. 1, dramatic, more than four-fold increases in perifollicular vessel size were observed during the anagen growth phase of the adult hair cycle, with a complete reduction to pre-anagen sizes during catagen and telogen phases. The percentage of perifollicular area covered by vessels increased from 4.1% to 15.9% during the anagen phase, and was reduced to 2.9% in telogen. Similar data were obtained during normal postnatal hair development. These results establish the adult murine hair follicle as the second organ, in addition to the female reproductive system (Iruela-Arispe et al. (1997) *Thrombosis and Haemostasis* 78:672–677), where physiologic modulation of angiogenesis can be studied. The short time period of 22 days during which a more than 4-fold expansion of vascular mass occurs, followed by complete regression of angiogenic vessels, makes the hair cycle a prime model system for studying the molecular mechanisms that control angiogenesis.

Association Between Angiogenesis and Hair Follicle Size and Hair Thickness

It was next examined whether the vascular remodeling observed during the anagen growth phase was temporally associated with increases in the size of hair follicles or in the thickness of the overlying epidermis, the dermis and the subcutis. Briefly, hematoxylin and eosin stainings were performed on 5-µm paraffin sections of tissues obtained from neonatal hair development studies and from the induced adolescent hair cycle. Five representative sections for each time point were analyzed, using a Nikon E-600 microscope, Epidermal, dermal and subcutaneous thickness were measured in digital images, using the IP-LAB software. The average length of individual hair follicles was determined by measuring the length of 50 hair follicles from the upper border of the epidermis to the lowest level of the hair follicle for each time point. The thickness of hair bulbs was measured at the level of the largest diameter.

The thickness of interfollicular epidermis significantly increased from day 1 to reach a maximum thickness of 54.5 µm on day 5, followed by a steep decline during mid- to late anagen with a further reduction during telogen. In contrast, dermal and subcutaneous thickness steadily increased from early anagen to reach a peak in late anagen, followed by a decline during catagen and telogen, coinciding with the cyclic changes of follicle length, and diameter of the hair bulb, as shown in FIG. 1. The exact temporal coincidence of the cyclic changes in follicle length, dermal and subcutaneous (but not epidermal) thickness, and perifollicular vascularization suggested that the stimulus leading to hair cycle-associated angiogenesis derived from the hair follicle itself or from the surrounding dermis and subcutis, but not from the interfollicular epidermis.

Role of VEGF in Hair Cycle Angiogenesis

To determine whether VEGF played a role in hair cycle angiogenesis, the spatiotemporal expression pattern of VEGF mRNA during hair cycling was examined by in situ hybridization. Briefly, in situ hybridization was performed on 5 µm paraffin sections as described Detmar et al. (1995) *J. Exp. Med.* 180:1141–1146, using antisense and sense single-stranded $^{35}$S-labeled RNA probes prepared from a 393-bp rat VEGF cDNA fragment that recognizes all known VEGF splice variants. VEGF mRNA expression was quantitated by counting individual photographic grains over follicular keratinocytes as described Brown et al. (1990) *J. Invest. Dermatol.* 104:744–749, and biopsies were scored as negative (0 grains per cell; score=0), weakly positive 2–5 grains per cell; score=1), moderately (6–10 grains per cell; score=2), or strongly positive (>10 grains per cell; score=3). Data are shown as percentage of maximum score.

Figure 2:
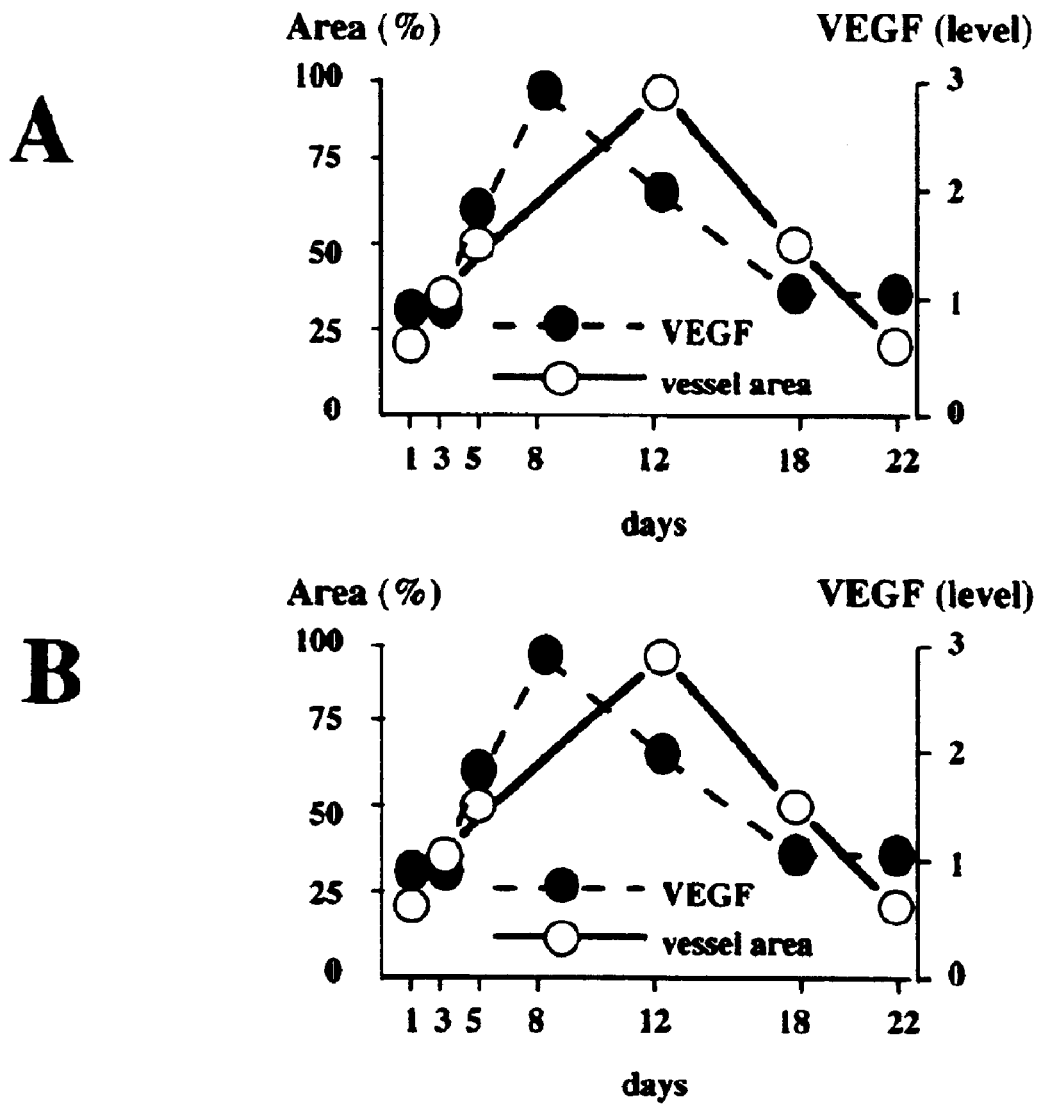
FIG. 2 shows the temporal correlation of follicular VEGF mRNA expression levels (filled circles) and perifollicular angiogenesis during the induced adult hair cycle (A) and the physiological first postnatal hair cycle (B). Relative vessel area (open circles) is expressed as a percentage of the maximum vessel area detected during late anagen.

Whereas little VEGF mRNA expression was detected in early anagen (day 1) hair follicles or in interfollicular epidermal keratinocytes, VEGF mRNA was highly expressed in follicular keratinocytes during mid-anagen (days 5 and 8), predominantly in the middle third of hair follicles, where perifollicular vascular remodeling was most prominent. In contrast, little or no VEGF mRNA expression was detected in the surrounding dermis, subcutis, and in dermal papilla cells. These results suggested follicular keratinocytes as the major source of VEGF during the anagen growth phase. The cyclic VEGF mRNA expression levels were compared with the cyclic changes of perifollicular vascularization, and it was found that modulations of VEGF expression preceded vascular changes by an interval of 3 to 4 days with a marked decrease of VEGF expression during late anagen, catagen, and telogen as shown in FIG. 2. These findings were confirmed by identical results obtained during postnatal follicle development, indicating that the increased angiogenesis during the depilation-induced adult hair cycle was not due to a wound response following depilation. Thus, the close spatiotemporal association of follicular VEGF expression and perifollicular angiogenesis strongly suggested an important role of VEGF in the control of hair vascularization.

In addition, 3-dimensional reconstruction experiments of CD31 stained sections data suggest that hair growth is associated with remodeling type angiogenesis, which involves enlargement and elongation of preexisting vessels, rather than a marked increase in the number of vesicles accompanying each hair follicle.

In Vivo Analysis of VEGF Expression on Hair Growth and Follicle Size

Figure 3:
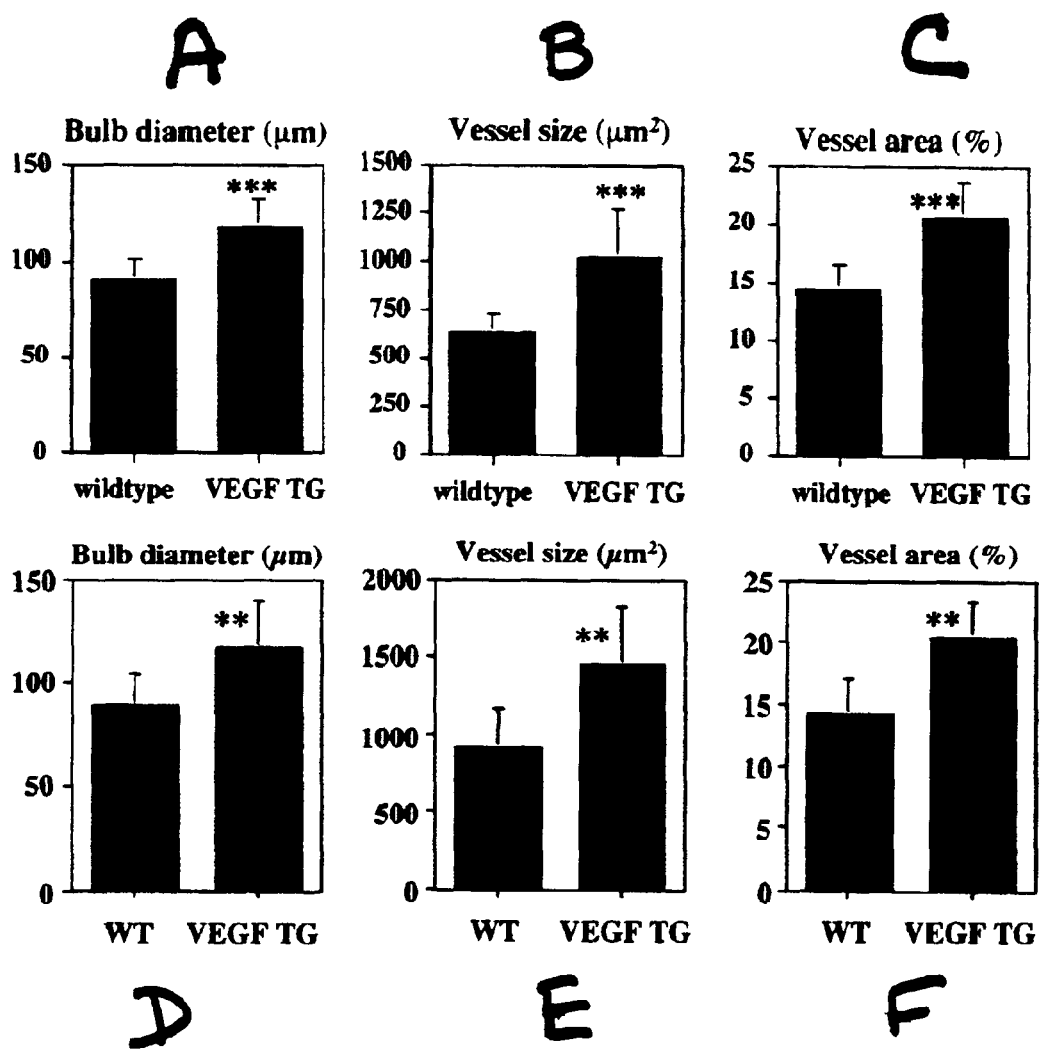
FIG. 3 shows measurements of hair bulb size (A and D), perifollicular vascularization (B and E), and vessel area (C and F) in VEGF transgenic mice as compared with wild-type littermates at day 12 (A, B, C) and day 15 (D, E, and F). $P<0.01$; $*P<0.001$, two-sided unpaired Student's t test.
Figure 4:
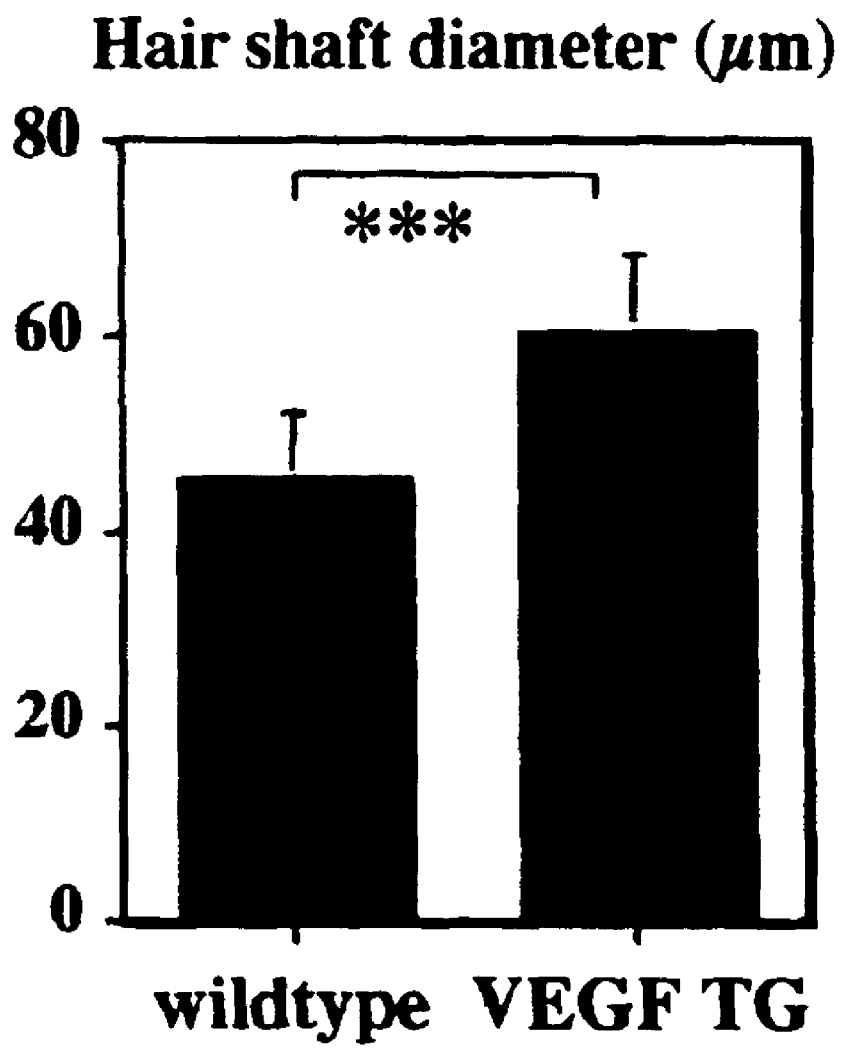
FIG. 4 is a quantitative analysis of hair shaft diameter, measured at the level of their greatest width, in VEGF transgenic mice (TG) compared to wild-type mice. Data are means+std. dev. (n=50 for each genotype) $***P<0.001$, two-sided unpaired Student's t test.

To investigate whether follicular VEGF expression directly promotes hair growth and vascularization, the hair cycle in a transgenic mouse model was studied for targeted overexpression of VEGF in basal epidermal keratinocytes and in outer root sheath keratinocytes of the hair follicle, using a keratin 14 promoter cassette. VEGF transgenic mice were established by using a keratin-14 promoter expression cassette to target murine VEGF 164 expression to basal epidermal keratinocytes and outer root sheath keratinocytes of hair follicles. The phenotypic characterization of VEGF transgenic mice has been previously reported in Detmar et al. (1998) *J. Invest. Dermatol.* 111:1–6. The induced hair cycle was studied in 5 eight-week-old VEGF transgenic mice and in 5 wildtype littermates as described above. Ten days after depilation, VEGF-overexpressing mice showed accelerated hair regrowth as compared with wildtype FVB littermates. After 11 days, these differences were more obvious, and the hair was longer and thicker in VEGF transgenic mice. Histological analysis revealed that hair follicles in VEGF transgenic mice were larger than in wildtype controls, most prominently at the level of the hair bulb. The increased size of hair follicles was mainly due to increased thickness of its epithelial components. As shown in FIG. 3, image analysis of hair bulbs at the level of Auger's critical line (level of maximum bulb diameter) revealed a more than 30% increase in diameter in VEGF transgenic mice. A significant, more than 40% increase in vessel sizes and total vascular mass was observed surrounding VEGF-overexpressing hair follicles as shown in FIG. 2. In addition, VEGF transgenic mice showed an increase in hair shaft diameter (FIG. 4). These findings strongly suggest that accelerated hair growth was a consequence of VEGF-mediated angiogenesis.

Figure 5:
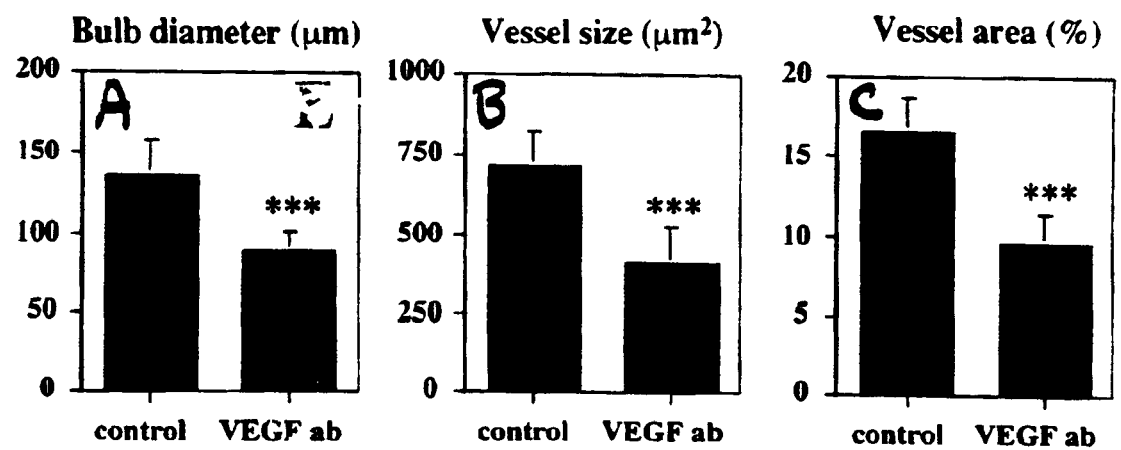
FIG. 5 demonstrates delayed hair regrowth in C57BL mice that were treated systemically with an anti-VEGF antibody.

It was next examined whether VEGF-mediated angiogenesis was essential for the timely growth of hair follicles during the anagen phase. Therefore, adult C57BL/6 mice were treated systemically with a neutralizing anti-VEGF antibody, and the hair cycle was induced by depilation one day after the first antibody application. Briefly, anagen was induced by depilation of 8-week-old female C57BL/6 mice. Eight mice each were injected intraperitoneally with 50 $\mu$g of a goat-anti-mouse VEGF neutralizing antibody (R&D Systems) or with 50 $\mu$g of normal goat IgG one day prior to depilation and thereafter twice weekly. Mice were sacrificed after 1, 5, 8, 12 and 18 days, and tissues were processed as described above. The neutralizing activity of the anti-VEGF antibody used was confirmed by its ability to completely inhibit VEGF-induced microvascular leakage in the skin of guinea pigs and of mice. Miles assays were performed in mice and guinea pigs as previously described in Senger et al. (1983) Science 219:983–985. Evans blue (1% in PBS, 100 $\mu$l per mouse; Sigma) was injected into the tail vein of anaesthetized mice at 24 h after intraperitoneal injection of 50 $\mu$g of anti-VEGF antibody or of 50 $\mu$g goat IgG. After 10 min, murine $VEGF_{164}$ (50 or 100 ng in 50 $\mu$l phosphate-buffered saline) was injected intradermally into the back skin, and leakage of protein-bound dye was detected as blue spots on the underside of the back skin surrounding the injection site. Guinea pigs were injected intradermally with 50 ng murine $VEGF_{164}$ either alone or premixed with different amounts of anti-VEGF antibody (1.5 $\mu$g, 5 $\mu$g, 15 $\mu$g), with antibody alone, or with phosphate-buffered saline. During the first 8 days after depilation, no differences in the macroscopic skin appearance were observed in anti-VEGF-treated mice. Thereafter, hair regrowth was delayed in VEGF-antibody-treated mice. After 12 days, hair regrowth was complete in control antibody-treated mice, whereas mice treated with the anti-VEGF antibody still showed bald spots and had an overall reduced hair growth. Histological analysis demonstrated that anagen hair follicles in anti-VEGF-treated mice were thinner with a more than 30% reduction in bulb diameters, mainly due to reduced thickness of the follicular epithelium, associated with a significant, more than 40% decrease of perifollicular vascularization (FIG. 5). These data demonstrate that inhibition of VEGF-mediated angiogenesis resulted in delayed hair growth and pronounced size reduction of the hair follicle.

Without wanting to be bound by theory, it is believed that a molecular mechanism by which the hair follicle meets its rapidly changing, high metabolic demands is through timed expression of VEGF by follicular keratinocytes, leading to increased perifollicular vascularization. The exact 22 day-period of the murine hair cycle, together with its experimental convenience, establish the hair follicle as an important new model system for experimental angiogenesis studies. In addition, these findings that targeted overexpression of VEGF in follicular keratinocytes resulted in accelerated hair regrowth provide evidence that induction of angiogenesis promotes hair growth. Taken together with the fact that VEGF blockade impaired hair regrowth and also resulted in reduced size of hair follicles, these findings clearly demonstrate that normal hair growth is VEGF-dependent. It remains to be examined whether systemic anti-angiogenic therapies for cancer and other diseases might interfere with normal human hair cycling and follicle size or with hair regrowth after polychemotherapy.

Impaired vascularization of the hair follicle has been previously suggested to play an important role in the pathogenesis of disorders characterized by hair loss, including androgenetic alopecia (male-pattern hair loss) where baldness is caused by miniaturization, but not loss or abolished cycling, of genetically predisposed follicles. See, e.g., Levy-Frankel (1931) Ann. Dermatol. 10:322–327; Cormia et al. (1961) Arch. Dermatol. 84:772–778. Based on the finding disclosed above, it is likely that some of these disorders may be potential targets for therapies aimed at increasing the vascular support of hair follicles.

Mouse Vibrissa Organ Culture System

Figure 6:
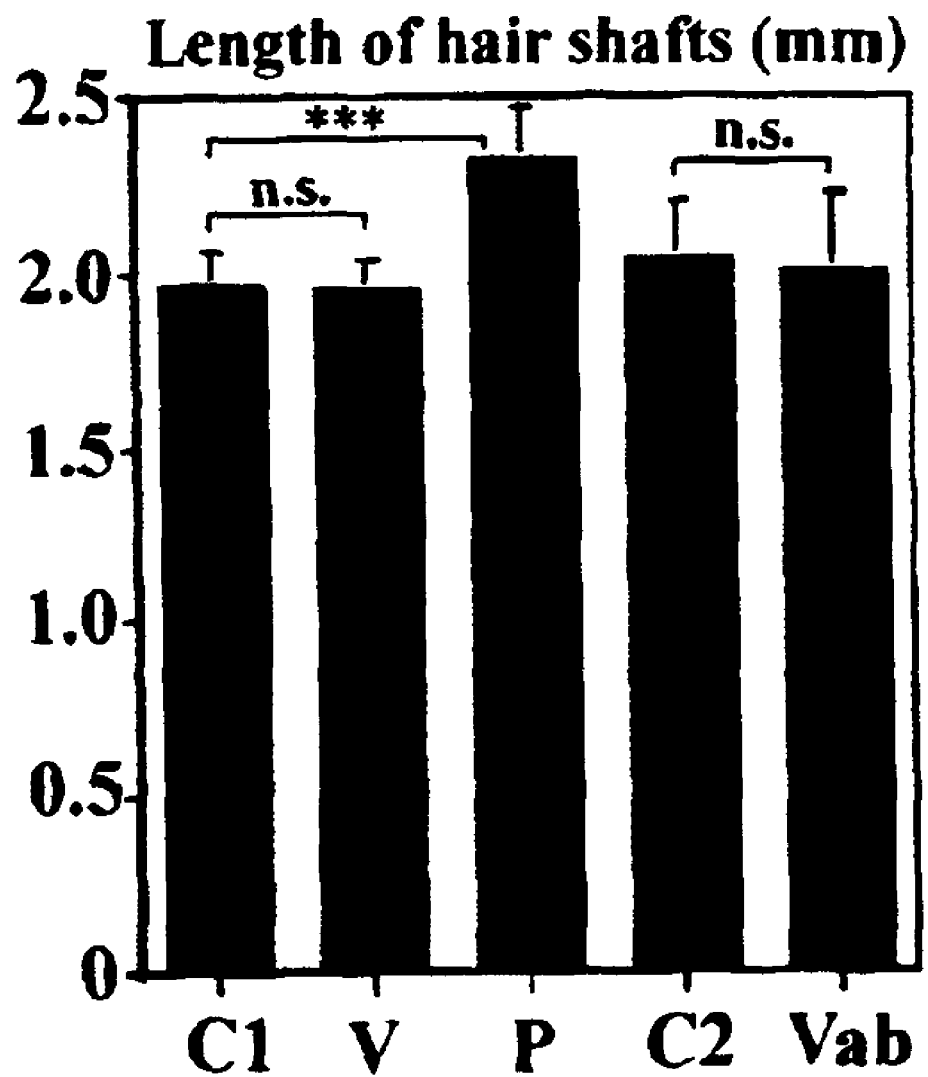
FIG. 6 demonstrates that VEGF has no effect on hair growth in organ culture of mouse vubrissae, in the absence of a vascular system. Treatment with VEGF (V) did not influence in vitro hair growth, as compared with untreated controls (C1). Treatment with a neutralizing anti-VEGF antibody (Vab) also did not influence in vitro hair growth, as compared with control-antibody treated follicles (C2). Addition of 5% FBS (P) was used as a positive contros=no significant difference; $***P<0.001$, two-sided unpaired Student's t test.

Whisker pads were isolated from three 5 week old female C57/BL mice and were shortly immersed in 70% ethanol in phosphate-buffered saline (PBS), followed by a 10 minute incubation in William's E medium containing 400 U/ml penicillin, 400 $\mu$g/ml streptomycin, and 1.0 $\mu$g/ml fungizone (all from GibcoBRL). Vibrissa follicles in the anagen growth phase were isolated under a dissecting microscope, and the part of the vibrissa shaft that extend over the epidermal surface was cut off. Vibrissa follicles were then incubated on Millapore membranes in William's E medium alone (n-8), in medium containing 50 ng/ml recombinant murine VEGF (R&D Systems; n=6), or medium containing 5% fetal bovine serum (FBS; n=8). The media were replaced by fresh media after 2 days, and the follicles were incubated over a total period of 4 days. After 4 days, the length of the outgrowing hair shafts was measured by image analysis of digital pictures, taken under a Nikon E600 microscope. There were no significant differences in the length of the hair shafts between control follicles (average hair growth was 1.963±0.101 mm) and VEGF-treated follicles (average growth was 1.959±0.086 mm), whereas follicles incubated in 5% FBS showed a significant increase in shaft length (average hair growth was 2.327±0.115 mm) (p<0.001, Student's t-test) (FIG. 6). This data demonstrates that under conditions of hair organ culture, in the absence of a functional vascular system, VEGF did not affect hair growth, suggesting that the effects of VEGF are mediated through induction of perifollicular angiogenesis.

In addition, whisker follicles were isolated and cultured as described above. Seven follicles were treated with 5 $\mu$g/ml of a goat anti-mouse VEGF neutralizing antibody (R&D Systems), and 8 follicles were treated with 5 $\mu$g/ml of normal goat IgG. After 4 days of culture, no significant differences in hair growth were observed between anti-VEGF treated follicles (average hair growth was 2.005±0.381 mm) and control goat IgG treated follicles (average hair growth was 2.051±0.398 mm) (FIG. 6). This data demonstrates that under conditions of hair organ culture, in the absence of a functioning vascular system, inhibition of VEGF did not affect hair growth.

VEGF Polypeptides and Nucleic Acid Sequences Encoding VEGF

VEGF polypeptides can be obtained in several ways including isolation of VEGF or expression of a sequence encoding VEGF by genetic engineering methods. For example, methods of recombinantly producing VEGF are known and described, e.g., in European Patent No.: 0 484 401, European Patent No.: 0 471 754 and U.S. Pat. No. 5,332,671. The nucleotide sequences of VEGF proteins from various species are known. See, e.g., European Patent No.: 0 506 477, U.S. Pat. Nos. 5,194,596, 5,332,671, 5,840,693, 5,928,939, 5,994,300.

Analogs of VEGF

Analogs can differ from naturally occurring VEGF in amino acid sequence or in ways that do not involve sequence, or both. Non-sequence modifications include in vivo or in vitro chemical derivatization of VEGF. Non-sequence modifications include changes in acetylation, methylation, phosphorylation, carboxylation, or glycosylation.

Preferred analogs include VEGF (or biologically active fragments thereof) whose sequences differ from the wild-type sequence by one or more conservative amino acid substitutions or by one or more non-conservative amino acid substitutions, deletions, or insertions which do not abolish the VEGF biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1
CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Production of Fragments and Analogs

Generation of Fragments

Various fragments of VEGF are known and described, for example, in U.S. Pat. No. 5,935,820.

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad Sci.* (1978) USA, 75: 5765).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecules, binding to natural ligands, e.g., a receptor or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with VEGF. These may include agonists, superagonists, and antagonists. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., a VEGF molecule or a fragment thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370–1371; and Goward et al. (1992) TIBS 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461).

A common approach uses the maltose receptor of E. coli (the outer membrane protein, LamB) as a peptide fusion partner (Charbit et al. (1986) EMBO 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp. 387–392), PhoE (Agterberg, et al. (1990) Gene 88, 37–45), and PAL (Fuchs et al. (1991) Bio/Tech 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) Bio/Tech. 6, 1080–1083). Surface proteins of other bacterial species have also served as peptide fusion partners. Examples include the Staphylococcus protein A and the outer membrane protease IgA of Neisseria (Hansson et al. (1992) J. Bacteriol. 174, 4239–4245 and Klauser et al. (1990) EMBO J. 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) Proc. Natl. Acad. Sci. U.S.A. 89-1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) Proc. Natl. Acad. Sci. U.S.A. 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are under-represented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding 1012 decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204, 357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject VEGF polypeptides to generate mimetics, e.g. peptide or non-peptide agents. See, for example, "Peptide inhibitors of human papillomavirus protein binding to retinoblastoma gene protein" European patent applications EP 0 412 762 and EP 0 031 080.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Fusion Proteins

Polypeptides for modulating the level of VEGF protein can be fused to another protein or portion thereof. For example, a VEGF protein or portion thereof, can be operably linked to another polypeptide moiety to enhance solubility. Examples of a protein which can be fused with VEGF or portions thereof include a plasma protein or fragment thereof, which can improve the circulating half life of VEGF. For example, the fusion protein can be a VEGF-immunoglobulin (Ig) fusion protein in which the VEGF sequence is fused to a sequence derived from the immunoglobulin superfamily. Several soluble fusion protein constructs have been disclosed wherein the extracellular domain of a cell surface glycoprotein is fused with the constant F(c) region of an immunoglobulin. For example, Capon et al. (1989) *Nature* 337(9):525–531, provide guidance on generating a longer lasting CD4 analog by fusing CD4 to an immunoglobulin (IgG1). See also, Capon et al., U.S. Pat. Nos. 5,116,964 and 5,428,130 (CD4-IgG fusion constructs); Linsley et al., U.S. Pat. No. 5,434,131 (CTLA4-IgG1 and B7-IgG1 fusion constructs); Linsley et al. (1991) *J. Exp. Med.* 174:561–569 (CTLA4-IgG1 fusion constructs); and Linsley et al. (1991) *J. Exp. Med* 173:721–730 (CD28-IgG1 and B7-IgG1 fusion constructs). Such fusion proteins have proven useful for modulating receptor-ligand interactions and reducing inflammation in vivo. For example, fusion proteins in which an extracellular domain of cell surface tumor necrosis factor receptor (TNFR) proteins has been fused to an immunoglobulin constant (Fc) region have been used in vivo. See, for example, Moreland et al (1997) *N. Engl. J. Med.* 337(3): 141–147; and, van der Poll et al. (1997) *Blood* 89(10):3727–3734).

Antibodies

The invention also includes antibodies specifically reactive with a subject VEGF polypeptides. Anti-protein/anti-peptide antisera or monoclonal antibodies can be made as described herein by using standard protocols (See, for example, *Antibodies: A Laboratory Manual* ed. by Harlow and Lane (Cold Spring Harbor Press: 1988)).

A VEGF protein, or a portion or fragment thereof, can be used as an immunogen to generate antibodies that bind VEGF using standard techniques for polyclonal and monoclonal antibody preparation. The full-length VEGF protein can be used or, alternatively, antigenic peptide fragments of VEGF can be used as immunogens.

Typically, VEGF or a VEGF peptide is used to prepare antibodies by immunizing a suitable subject, (e.g., rabbit, goat, mouse or other mammal) with the immunogen. An appropriate immunogenic preparation can contain, for example, a recombinant VEGF peptide, or a chemically synthesized VEGF peptide. See, e.g., U.S. Pat. No. 5,460,959; and co-pending U.S. applications U.S. Ser. Nos. 08/334,797; 08/231,439; 08/334,455; and 08/928,881 which are hereby expressly incorporated by reference in their entirety. The nucleotide and amino acid sequences of VEGF are known. The preparation can further include an adjuvant, such as Freund's complete or incomplete adjuvant, or similar immunostimulatory agent. Immunization of a suitable subject with an immunogenic VEGF preparation induces a polyclonal anti-VEGF antibody response.

Anti-VEGF antibodies or fragments thereof can be used to inhibit the levels of VEGF protein. Examples of anti-VEGF antibody fragments include F(v), Fab, Fab' and F(ab')$_2$ fragments which can be generated by treating the antibody with an enzyme such as pepsin. The term "monoclonal antibody" or "monoclonal antibody composition", as used herein, refers to a population of antibody molecules that contain only one species of an antigen binding site capable of immunoreacting with a particular epitope of VEGF. A monoclonal antibody composition thus typically displays a single binding affinity for a particular VEGF protein with which it immunoreacts.

Additionally, anti-VEGF antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., *Science* 240:1041–1043, 1988; Liu et al., *PNAS* 84:3439–3443, 1987; Liu et al., *J. Immunol.* 139:3521–3526, 1987; Sun et al. *PNAS* 84:214–218, 1987; Nishimura et al., *Canc. Res.* 47:999–1005, 1987; Wood et al., *Nature* 314:446–449, 1985; and Shaw et al., *J. Natl. Cancer Inst.* 80:1553–1559, 1988); Morrison, S. L., *Science* 229:1202–1207, 1985; Oi et al., *BioTechniques* 4:214, 1986; Winter U.S. Pat. No. 5,225,539; Jones et al., *Nature* 321:552–525, 1986; Verhoeyan et al., *Science* 239:1534, 1988; and Beidler et al., *J. Immunol.* 141:4053–4060, 1988.

In addition, a human monoclonal antibody directed against VEGF can be made using standard techniques. For example, human monoclonal antibodies can be generated in transgenic mice or in immune deficient mice engrafted with antibody-producing human cells. Methods of generating such mice are describe, for example, in Wood et al. PCT publication WO 91/00906, Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication 94/25585; Rajewsky et al. Pct publication WO 94/04667; Ditullio et al. PCT publication WO 95/17085; Lonberg, N. et al. (1994) *Nature* 368:856–859; Green, L. L. et al. (1994) *Nature Genet.* 7:13–21; Morrison, S. L. et al. (1994) *Proc. Natl. Acad. Sci. USA* 81:6851–6855; Bruggeman et al. (1993) *Year Immunol* 7:33–40; Choi et al. (1993) *Nature Genet.* 4:117–123; Tuaillon et al. (1993) *PNAS* 90:3720–3724; Bruggeman et al. (1991) *Eur J Immunol* 21:1323–1326); Duchosal et al. PCT publication WO 93/05796; U.S. Pat. No. 5,411,749; McCune et al. (1988) *Science* 241:1632–1639), Kamel-Reid et al. (1988) *Science* 242:1706; Spanopoulou (1994) *Genes & Development* 8:1030–1042; Shinkai et al. (1992) *Cell* 68:855–868). A human antibody-transgenic mouse or an immune deficient mouse engrafted with human antibody-producing cells or tissue can be immunized with VEGF or an antigenic VEGF peptide and splenocytes from these immunized mice can then be used to create hybridomas. Methods of hybridoma production are well known.

Human monoclonal antibodies against VEGF can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) *J. Mol. Biol.* 222:581–597; and Griffiths et al. (1993) *EMBO J* 12:725–734. In addition, a combinatorial library of antibody variable regions can be generated by mutating a known human antibody. For example, a variable region of a human antibody known to bind VEGF, can be mutated, by for example using randomly altered mutagenized oligonucleotides, to generate a library of mutated variable regions which can then be screened to bind to VEGF. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) *Proc. Nat'l Acad. Sci. USA* 89:4457–4461.

The immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) *Bio/Technology* 9:1370–1372; Hay et al. (1992) Hum Antibod Hybridomas 3:81–85; Huse et al. (1989) *Science* 246:1275–1281; Griffths et al. (1993) supra; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982. Once displayed on the surface of a display package (e.g., filamentous phage), the antibody library is screened to identify and isolate packages that express an antibody that binds VEGF. In a preferred embodiment, the primary screening of the library involves panning with an immobilized VEGF and display packages expressing antibodies that bind immobilized VEGF are selected.

Antisense VEGF Nucleic Acid Sequences

Nucleic acid molecules which are antisense to a nucleotide encoding VEGF can be used as an agent which inhibits VEGF expression. An "antisense" nucleic acid includes a nucleotide sequence which is complementary to a "sense" nucleic acid encoding VEGF, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire VEGF coding strand, or to only a portion thereof. For example, an antisense nucleic acid molecule which antisense to the "coding region" of the coding strand of a nucleotide sequence encoding VEGF can be used.

The coding strand sequences encoding VEGF are known. Given the coding strand sequences encoding VEGF, antisense nucleic acids can be designed according to the rules of Watson and Crick base pairing. The antisense nucleic acid molecule can be complementary to the entire coding region of VEGF mRNA, but more preferably is an oligonucleotide which is antisense to only a portion of the coding or noncoding region of VEGF mRNA. For example, the antisense oligonucleotide can be complementary to the region surrounding the translation start site of VEGF mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Administration

An agent which modulates the level of expression of a VEGF protein can be administered to a subject by standard methods. For example, the agent can be administered by any of a number of different routes including intravenous, intradermal, subcutaneous, oral (e.g., inhalation), transdermal (topical), and transmucosal. In one embodiment, the VEGF modulating agent can be administered topically.

The agent which modulates VEGF protein levels, e.g., nucleic acid molecules, VEGF polypeptides, fragments or analogs, VEGF modulators, and anti-VEGF antibodies (also referred to herein as "active compounds") can be incorporated into pharmaceutical compositions suitable for administration to a subject, e.g., a human. Such compositions typically include the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a VEGF polypeptide or anti-VEGF antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Such transdermal formulations can by applied to the skin to promote or inhibit hair growth.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., PNAS 91:3054–3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

The agent which modulates the level of VEGF protein can be administered by locally administration, e.g., topical administration. The agent can be applied once or it can be administered continuously, e.g., the agent is administered with sufficient frequency such that the affect on the VEGF protein level is maintained for a selected period, e.g., 5, 10, 20, 30, 50, 90, 180, 365 days or more. The administration of an agent which modulates, e.g., increases or inhibits, the level of a VEGF protein, e.g., a VEGF polypeptide or an anti-VEGF antibody, can also be repeated.

Transition Metals

Transition metal ions have been shown to enhance expression of the VEGF gene thereby increasing VEGF protein levels. See U.S. Pat. No. 5,480,975. Thus, in one aspect, a transition metal ion can be used to promote hair growth and/or thickening by increasing expression of VEGF.

The transition metals are the group consisting of the fourth, fifth and sixth levels of the periodic table and which fill the d orbital. They include such elements as Ni, Co, Mn, Zn, V, Cr, Fe, Cu, Mo, etc. The preferred candidate metal ions for use are manganese, cobalt and nickel.

Selection of other appropriate metal ions involves determining whether, and at what level, the ion will induce VEGF expression. Particularly for systemic applications, selection also involves a review of toxicity. Suitable techniques for those determinations are provided below in U.S. Pat. No. 5,480,795. Preferred ions are those with a substantial range between VEGF induction and toxicity.

The transition metal can be administered internally (systemic or local administration) in the form of a salt or free ion in a biologically compatible tablet or capsule, gel, or liquid, or it can be administered externally in the form of a biologically compatible powder, salve, liquid, or transdermal patch. Any physiologically acceptable anion such as chloride, sulfate, etc., can be included in the composition.

Appropriate release rates and dosages can be determined in order to affect the targeted tissue without substantial systemic effect. For example, these parameters can be determined as described in U.S. Pat. No. 5,480,795.

Gene Therapy

The gene constructs of the invention can also be used as a part of a gene therapy protocol to deliver nucleic acids encoding either an agonistic or antagonistic form of a VEGF polypeptide. The invention features expression vectors for in vivo transfection and expression of a VEGF polypeptide in particular cell types so as to reconstitute the function of, or alternatively, antagonize the function of a VEGF polypeptide in a cell in which that polypeptide is misexpressed. Expression constructs of VEGF polypeptides, may be administered in any biologically effective carrier, e.g. any formulation or composition capable of effectively delivering the VEGF gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a VEGF polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad Sci. USA* 88:8039–8043; Ferry et al. (1991) *Proc. Natl. Acad Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad Sci. USA* 89:10892–10895; Hwu et al. (1993) *J. Immunol.* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97–129). It is also one of the few viruses that may integrate its DNA into non-dividing cells, and exhibits a high frequency of stable integration (see for example Flotte et al. (1992) *Am. J. Respir. Cell. Mol Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a VEGF polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject VEGF gene by the targeted cell. Exemplary gene delivery systems of this type include liposomal derived systems, poly-lysine conjugates, and artificial viral envelopes. Other embodiments include plasmid injection systems such as are described in Meuli et al. (2001) *J Invest Dermatol.* 116(1):131–135; Cohen et al. (2000) *Gene Ther* 7(22):1896–905; or Tam et al. (2000) *Gene Ther* 7(21):1867–74.

In a representative embodiment, a gene encoding a VEGF polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic VEGF gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Cell Therapy

VEGF can also be increased in a subject by introducing into a cell, e.g., a fibroblast or a keratinocyte, e.g., a follicular keratinocyte, a nucleotide sequence that modulates the production of VEGF, e.g., a nucleotide sequence encoding a VEGF polypeptide or functional fragment or analog thereof, a promoter sequence, e.g., a promoter sequence from a VEGF gene or from another gene; an enhancer sequence, e.g., 5' untranslated region (UTR), e.g., a 5' UTR from a VEGF gene or from another gene, a 3' UTR, e.g., a 3' UTR from a VEGF gene or from another gene; a polyadenylation site; an insulator sequence; or another sequence that modulates the expression of VEGF. The cell can then be introduced into the subject.

Primary and secondary cells to be genetically engineered can be obtained form a variety of tissues and include cell types which can be maintained propagated in culture. For example, primary and secondary cells include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient) of the same species or another species (e.g., mouse, rat, rabbit, cat, dog, pig, cow, bird, sheep, goat, horse).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding VEGF, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous VEGF sequence. An exogenous nucleic acid sequence can be introduced into a primary or secondary cell by homologous recombination as described, for example, in U.S. Pat. No. 5,641,670, the contents of which are incorporated herein by reference.

The transfected primary or secondary cells may also include DNA encoding a selectable marker which confers a selectable phenotype upon them, facilitating their identification and isolation. Methods for producing transfected primary and secondary cells which stably express exogenous synthetic DNA, clonal cell strains and heterogeneous cell strains of such transfected cells, methods of producing the clonal heterogeneous cell strains, and methods of treating or preventing an abnormal or undesirable condition through the use of populations of transfected primary or secondary cells are part of the present invention.

Transfection of Primary or Secondary Cells of Clonal or Heterogeneous Cell Strains Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. The exogenous nucleic acid sequence can optionally include DNA encoding a selectable marker. The exogenous nucleic acid sequence and selectable marker-encoding DNA can either be on separate constructs or on a single construct. An appropriate quantity of DNA is used to ensure that at least one stably transfected cell containing and appropriately expressing exogenous DNA is produced. In general, approximately 0.1 to 500 $\mu$g of DNA is used.

As used herein, the term "transfection" includes a variety of techniques for introducing an exogenous nucleic acid into a cell including calcium phosphate or calcium chloride precipitation, microinjection, DEAE-dextrin-mediated transfection, lipofection or electrophoration.

Electroporation is carried out at approximate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. Total DNA of approximately 0.1 to 500 µg is generally used.

Methods such as calcium phosphate precipitation, modified calcium phosphate precipitation an polybrene precipitation, liposome fusion and receptor-mediated gene delivery can also be used to transect cells. Primary or secondary cells can also be transfected using microinjection. A stably, transfected cell can then be isolated and cultured and sub cultivated, under culturing conditions and for sufficient time to propagate stably transfected secondary cells an produce a clonal cell strain of transfected secondary cells. Alternatively, more than one transfected cell is cultured and sub cultured, resulting in production of a heterogeneous cell strain.

Transfected primary or secondary cells undergo sufficient number doubling to produce either a clonal cell strain or a heterogeneous cell strain of sufficient size to provide the therapeutic protein to an individual in effective amounts. In general, for example, 0.1 $cm^2$ of skin is biopsies and assumed to contain 1,000,000 cells; one cell is used to produce a clonal cell strain and undergoes approximately 27 doublings to produce 100 million transfected secondary cells. If a heterogeneous cell strain is to be produced from an original transfected population of approximately 1000,000 cells, only 10 doublings are needed to produce 100 million transfected cells.

The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient. The put these factors in perspective, to deliver therapeutic levels of human growth hormone in an otherwise healthy 10 kg patient with isolated growth hormone deficiency, approximately one to five hundred million transfected fibroblast would be necessary (the volume of these cells is about that of the very tip of the patient's thumb).

Implantation of Clonal Cell Strain or Heterogeneous Cell Strain of Transfected Secondary Cells The transfected cells, e.g., cells produced as described herein, can be introduced into an individual to whom the product is to be delivered. The clonal cell strain or heterogeneous cell strain is then introduced into an individual. Various routed of administration and various sites (e.g., renal sub capsular, subcutaneous, central nervous system (including intrathecal), intravascular, intrahepatic, intrasplanchnic, intraperitoneal (including intraomental), intramuscularly implantation) can be used. One implanted in individual, the transfected cells produce the product encoded by the heterologous DNA or are affected by the heterologous DNA itself. For example, an individual who suffers from hair loss is a candidate for implantation of VEGF producing cells.

The individual can have a small skin biopsy performed; this is a simple procedure which can be performed on an outpatient basis. The piece of skin is taken, for example, from under the arm and can require about one minute to remove. The sample is processed, resulting in isolation of the patient's cell (e.g., fibroblasts) and genetically engineered to produce VEGF or another protein or molecule that induces the production of VEGF. Based on the age, weight, and clinical condition of the patient, the required number of cells are grown in large-scale culture. The entire process should require 4–6 weeks and, at the end of that time, the appropriate number of genetically engineered cells are introduced into the individual, once again as an outpatient (e.g., by injecting them back under the patient's skin, e.g., on the scalp or face). The patient is now capable of producing VEGF which can ameliorate symptoms of hair loss.

For some, this will be a one-time treatment and, for others, multiple cell therapy treatments will be required.

As this example suggests, the cells used will generally be patient-specific genetically engineered cells. It is possible, however, to obtain cells from another individual of the same species or from a different species. Use of such cells might require administration of an immunosuppressant, alteration of histocompatibility antigens, or use of a barrier device to prevent rejection of the implanted cells.

Transfected primary or secondary cells can be administered alone or in conjunction with a barrier or agent for inhibiting immune response against the cell in a recipient subject. For example, an immunosuppressive agent can be administered to a subject to inhibit or interfere with normal response in the subject. Preferably, the immunosuppressive agent is an immunosuppressive drug which inhibits T cell/or B cell activity in a subject. Examples of such immunosuppressive drugs commercially available (e.g., cyclosporin A is commercially avail for Sandoz Corp. East Hanover, N.J.).

An immunosuppressive agent e.g., drug, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) *N. Engl. J. Med* 327:1549; Spencer et al. (1992) *N. Engl. J. Med.* 327:1541' Widner et al. (1992) *n. Engl. J. Med.* 327:1556). Dosage values may vary according to factors such as the disease state, age, sex, and weight of the individual.

Another agent with can be used to inhibit T cell activity in a subject is an antibody, or fragment of derivative thereof. Antibodies capable of depleting or sequestering T cells in vivo are known in the art. Polyclonal antisera can be used, for example, anti-lymphocyte serum. Alternatively, one or more monoclonal antibodies can be used. Preferred T cell depleting antibodies include monoclonal antibodies which bind to CD2, CD3, CD4, CD8, CD40, CD40, ligand on the cell surface. Such antibodies are known in the art and are commercially available, for example, form American Type Culture Collection. A preferred antibody for binding CD3 on human T cells is OKT3 (ATCC CRL 8001).

An antibody which depletes, sequesters or inhibits T cells within a recipient subject can be administered in a dose for an appropriate time to inhibit rejection of cells upon transplantation. Antibodies are preferably administered intravenously in a pharmaceutically acceptable carrier of diluent (e.g., saline solution).

Another way of interfering with or inhibiting an immune response to the cells in a recipient subject is to use an immunobarrier. An "immunobarrier" as used herein, refers to a device which serves as a barrier between the administered cell and cells involved in immune response in a subject. For example, the cells can be administered in an implantable device. An implantable device can include the cells contained within a semi-permeable barrier, i.e., one which lets nutrients and the product diffuse in and out of the barrier but which prevents entry or larger immune system components, e.g., antibodies or complement. An implantable device typically includes a matrix, e.g., a hydrogel, biocompatible mesh, or core in which cells are disposed. Optionally, a semi permeable coating can enclose the gel. If disposed within the gel core, the administered cells should be sequestered from the cells of the immune system and should be cloaked from the cells and cytotoxic antibodies of the host. Preferably, a permselective coating such as PLL or PLO is used. The coating often has a porosity which prevents components of the recipient's immune system from entering and destroying the cells within the implantable device.

Many methods for encapsulating cells are known in the art. For example, encapsulation using a water soluble gum to obtain a semi-permeable water insoluble gel to encapsulate cells for production and other methods of encapsulation are disclosed in U.S. Pat. No. 4,352,883. Other implantable devices which can be used are disclosed in U.S. Pat. Nos. 5,084,350, 5,427.935, WO 95/19743 published Jul. 27, 1995, U.S. Pat. Nos. 5,545,423, 4,409,331, 4,663,286, and European Patent No. 301,777.

An advantage of the use of transfected or secondary cells is that by controlling the number of cells introduced into an individual, one can control the amount of the protein delivered to the body. In addition, in some cases, it is possible to remove the transfected cells of there is no longer a need for the product. A further advantage of treatment by use of transfected primary or secondary cells of the present invention is that production of the therapeutic product can be regulated, such as through the an administration of zinc, steroids or an agent which affects transcription of a protein, product or nucleic acid product or affects the stability of a nucleic acid product.

Other Embodiments

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patents and references cited herein are incorporated in their entirety by reference. Other embodiments are within the following claims.

We claim:

1. A method of selecting a compound that modulates hair growth or hair thickness, comprising:

providing a test compound; and providing a follicular keratinocyte;

treating the follicular keratinocyte with the test compound; and evaluating the ability of the test compound to modulate VEGF in the follicular keratinocyte, wherein if the test compound modulates VEGF compared to a control, said test compound is selected, thereby selecting a compound that modulates hair growth or hair thickness.

2. The method of claim 1, wherein the test compound is a polypeptide.

3. The method of claim 1, wherein the test compound is a fragment of VEGF.

4. The method of claim 1, wherein the test compound is an analog of VEGF.

5. The method of claim 1, wherein the test compound is a peptide mimetic.

6. The method of claim 1, wherein the test compound is a fusion protein.

7. The method of claim 1, wherein the test compound is an antibody.

8. The method of claim 1, wherein the test compound is an antisense VEGF nucleic acid sequence.

9. The method of claim 1, wherein the test compound is a transition metal.

10. The method of claim 1, wherein the evaluating step comprises evaluating the level of VEGF protein.

11. The method of claim 1, wherein the evaluating step comprises evaluating the level of VEGF RNA.

12. The method of claim 1, wherein a test compound that increases VEGF is selected as a compound that increases hair growth or thickness.

13. The method of claim 1, wherein a test compound that decreases VEGF is selected as a compound that decreases hair growth or thickness.

14. A method of selecting a compound that modulates hair thickness, comprising:

providing a test compound;

providing a follicular keratinocyte;

treating the follicular keratinocyte with the test compound; and evaluating the ability of the test compound to modulate VEGF in the follicular keratinocyte, wherein if the test compound modulates VEGF compared to a control, said test compound is selected, thereby selecting a compound that modulates hair thickness.

15. The method of claim 14, wherein the test compound is a polypeptide.

16. The method of claim 14, wherein the test compound is a fragment of VEGF.

17. The method of claim 14, wherein the test compound is an analog of VEGF.

18. The method of claim 14, wherein the test compound is a peptide mimetic.

19. The method of claim 14, wherein the test compound is a fusion protein.

20. The method of claim 14, wherein the test compound is an antibody.

21. The method of claim 14, wherein the test compound is an antisense VEGF mucleic acid sequence.

22. The method of claim 14, wherein the test compound is a transition metal.

23. The method of claim 14, wherein the evaluating step comprises evaluating the level of VEGF protein.

24. The method of claim 14, wherein the evaluating step comprises evaluating the level of VEGF RNA.

25. The method of claim 14, wherein a test compound that increases VEGF is selected as a compound that increases hair thickness.

26. The method of claim 14, wherein a test compound that decrease VEGF is selected as a compound that decreases hair thickness.

* * * * *